US006211202B1

(12) United States Patent
Canada et al.

(10) Patent No.: US 6,211,202 B1
(45) Date of Patent: Apr. 3, 2001

(54) 2-METHOXYIMINO-2-(PYRIDINYLOXYMETHYL) PHENYL ACETAMIDES WITH SUBSTITUTED KETAL DERIVATIVES ON THE PYRIDINE RING

(75) Inventors: Emily J. Canada, Indianapolis; Christopher S. Galka, Carmel; Dave D. Johnson, Indianapolis; Neil Kirby, Carmel; Irene M. Morrison, Indianapolis; Bassam S. Nader, Fishers; Jim M. Renga, Indianapolis, all of IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 09/192,139

(22) Filed: Nov. 13, 1998

Related U.S. Application Data

(60) Provisional application No. 60/065,703, filed on Nov. 14, 1997.

(51) Int. Cl.[7] .......................... A01N 43/40; C07D 407/04
(52) U.S. Cl. .................. 514/336; 546/281.7; 546/282.4; 546/283.7
(58) Field of Search .......................... 546/283.7; 514/336

(56) References Cited

U.S. PATENT DOCUMENTS

| 5,185,342 | 2/1993 | Hayase et al. . |
| 5,334,577 | 8/1994 | Wenderoth et al. . |
| 5,371,222 | 12/1994 | Hayase et al. . |
| 5,371,223 | 12/1994 | Hayase et al. . |
| 5,401,877 | 3/1995 | Hayase et al. . |
| 5,439,911 | 8/1995 | Ohtsuka et al. . |

FOREIGN PATENT DOCUMENTS

| 4312637 A1 | 10/1994 | (DE) . |
| 0398692 A2 | 11/1990 | (EP) . |
| 04182461 | 6/1992 | (JP) . |
| WO 95/32182 | 11/1995 | (WO) . |
| WO 96/20164 | 7/1996 | (WO) . |
| WO 97/30032 | 8/1997 | (WO) . |

Primary Examiner—Patricia L. Morris
(74) Attorney, Agent, or Firm—Carl D. Corvin; Kenneth L. Loertscher

(57) ABSTRACT

The present invention provides novel 2-methoxyimino-2-(pyridinyloxymethyl)phenyl acetamide compounds with substituted ketal substituents on the pyridine ring, their use as fungicidal compounds, and their use in fungicidal compositions comprising at least one of the 2-methoxyimino-2-(pyridinyloxymethyl)phenyl acetamide compounds as the active ingredient.

14 Claims, No Drawings

2-METHOXYIMINO-2-(PYRIDINYLOXYMETHYL) PHENYL ACETAMIDES WITH SUBSTITUTED KETAL DERIVATIVES ON THE PYRIDINE RING

CROSS-REFERENCE TO RELATED APPLICATION

This application claims the benefit of U.S Provisional Application No. 60/065,703, filed Nov. 14 1997.

BACKGROUND OF THE INVENTION

The present invention provides novel 2-methoxyimino-2-(pyridinyloxymethyl)phenyl acetamide compounds with substituted ketal substituents on the pyridine ring, their use as fungicidal compounds, and their use in fungicidal compositions comprising at least one of the 2-methoxyimino-2-(pyridinyloxymethyl)phenyl acetamide compounds as the active ingredient.

SUMMARY OF THE INVENTION

This invention provides novel 2-methoxyimino-2-(pyridinyloxymethyl)phenyl acetamide compounds of formula (1), below

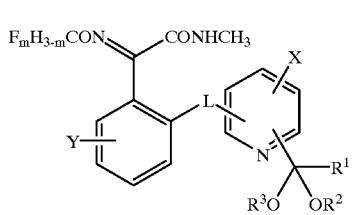

Formula (1)

wherein
  m is an integer 0–3;
  Y is H, halogen, $C_{1-4}$ alkyl, halo-$C_{1-4}$ alkyl, $C_{1-4}$ alkoxy, halo-$C_{1-4}$ alkoxy, or $C_{1-4}$ alkylthio;
  X is H, $C_{1-6}$ alkyl, $C_{1-6}$ alkoxy, halo-$C_{1-6}$ alkyl, halo-$C_{1-6}$ alkoxy, halo, nitro, $C_{1-6}$ alkoxycarbonyl, cyano, $C_{1-6}$ alkylthio, or halo-$C_{1-6}$ alkylthio;
  $R^1$ is H, $C_{1-6}$ alkyl optionally substituted with one or more halogens, $C_{3-7}$ cycloalkyl optionally substituted with one or more halogens, $C_{2-6}$ alkenyl, $C_{2-6}$ alkynyl, or aryl or heteroaryl wherein the aryl or heteroaryl groups are optionally substituted by one or more of any of the groups selected from halogens, $C_{1-6}$ alkyl, $C_{3-7}$ cycloalkyl, halo-$C_{1-6}$ alkoxy, $C_{2-6}$ alkenyl, halo-$C_{2-6}$ alkenyl, $C_{2-6}$ alkynyl, cyano, $C_{1-6}$ alkoxy, nitro, aryl, substituted aryl, or heteroaryl;
  $R^2$, $R^3$ are each separately $C_{1-6}$ alkyl, $C_{3-7}$ cycloalkyl or $R^2$, $R^3$ together form a $C_{2-6}$ optionally substituted alkylene chain (whereby a cyclic structure is formed by the alkylene chain and the adjacent oxygen atoms), preferably a $C_{2-3}$ alkylene chain, wherein the optional substitution of the alkylene chain is with one or more of any of the following groups, $C_{1-4}$ alkyl optionally substituted with one or more halogens; or a phenyl group optionally substituted with one or more of any of the following groups, $C_{1-6}$ alkyl, $C_{1-6}$ alkoxy, halo-$C_{1-6}$ alkyl, halo-$C_{1-6}$ alkoxy, halo, nitro, $C_{1-6}$ alkoxycarbonyl, or cyano; and
  L is —O—, —$CH_2$—, —$SO_n$—, —$CH_2O$—, —$OCH_2$—, —$CH_2S$—, —$SCH_2$—, —CH=CH—, —C≡C—, or

wherein n is an integer 0–2.

The present invention also provides compositions comprising one or more compounds of formula (1) in combination with phytologically-acceptable carriers and/or diluents. Methods for the use of compounds of formula (1) and compositions comprising one or more compounds of formula (1) are also provided.

DETAILED DESCRIPTION OF THE INVENTION

Throughout this document, all temperatures are given in degrees Celsius and all percentages are weight percentages, unless otherwise stated.

The term "halogen" or "halo" refers to F, Cl, I, or Br.

The term "alkyl", "alkenyl", or "alkynyl" refers to a straight chain or branched chain carbon radical containing the designated number of carbon atoms.

The term "alkoxy" refers to a straight or branched chain alkoxy group.

The term "haloalkyl" refers to a straight or branched alkyl group substituted with one or more halogens. The term "haloalkoxy" refers to an alkoxy group substituted with one or more halogens.

The term "aryl" or "Ph" refers to a phenyl group. The term "substituted aryl" refers to a phenyl group substituted with $C_{1-6}$ alkyl, $C_{1-6}$ alkoxy, halo-$C_{1-6}$ alkyl, halo-$C_{1-6}$ alkoxy, halo, nitro, $C_{1-6}$ alkoxycarbonyl, or cyano. The term "heteroaryl" refers to pyridyl, pyrimidinyl, thienyl, quinolyl, furyl, pyrazinyl or pyridazinyl.

The term "Me" refers to a methyl group. The term "Et" refers to an ethyl group. The term "Pr" refers to a propyl group. The term "Bu" refers to a butyl group.

The term "EtOAc" refers to ethyl acetate.

The term "ppm" refers to parts per million. The term "psi" refers to pounds per square inch.

The term "M.P." refers to melting point. The term "bp" refers to boiling point.

While all the compounds of this invention have fungicidal activity, certain classes of compounds may be preferred for reasons such as, for example, greater efficacy or ease of synthesis.

A preferred class includes those compounds of formula (2), below

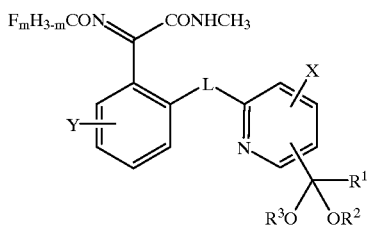

Formula (2)

wherein the substituents are as defined in formula (1), above.

A more preferred class includes those compounds of formula (3), below

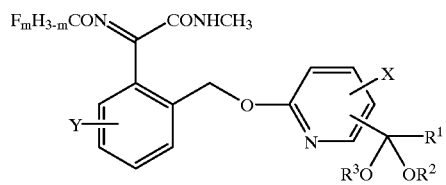

Formula (3)

wherein the substituents are as defined in formula (1), above.

A next more preferred class includes those compounds of formula (4), below

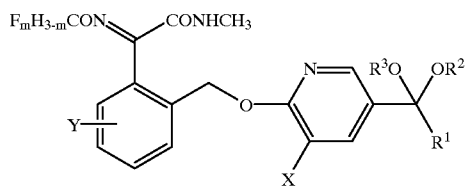

Formula (4)

wherein the substituents are as defined in formula (1), above.

A next more preferred class includes those compounds of formula (5), below

Formula (5)

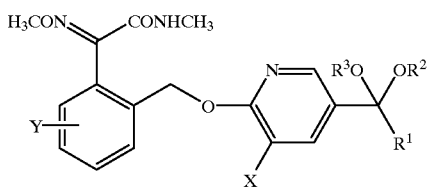

wherein the substituents are as defined in formula (1), above.

A next more preferred class includes those compounds of formula (6), below

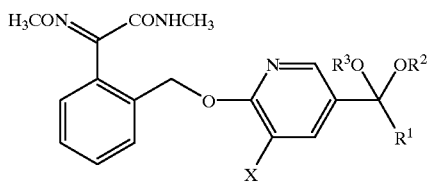

Formula (6)

wherein the substituents are as defined in formula (1), above.

A particularly preferred class includes those compounds of formula (7), below

Formula (7)

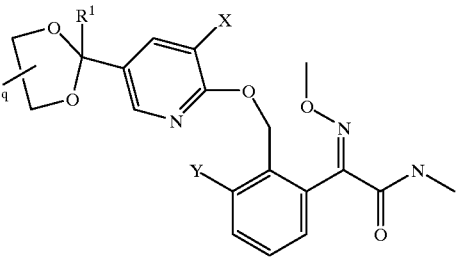

wherein X, Y and $R^1$ are as defined for formula (1) above; and $R^4$ is a $C_{1-4}$ alkyl optionally substituted with one or more halogens, or a phenyl group optionally substituted with one or more of any of the following groups, $C_{1-6}$ alkyl, $C_{1-6}$ alkoxy, halo-$C_{1-6}$ alkyl, halo-$C_{1-6}$ alkoxy, halo, nitro, $C_{1-6}$ alkoxycarbonyl, or cyano; and q is an integer 0–4.

Preferred compounds are the compounds of formula (7) wherein q is 0.

Also preferred are compounds of formula (7) wherein

Y is H, F or Cl;

X is H, Cl or Me;

$R^1$ is H, $C_{1-6}$ alkyl or a phenyl optionally substituted with one or more of any of the following, Cl, F, $C_{1-6}$ alkyl, preferably methyl, $C_{1-6}$ alkoxy, halo-$C_{1-6}$ alkyl, preferably trifluoromethyl, or halo-$C_{1-6}$ alkoxy, preferably trifluoromethoxy; and q is 0.

The compounds of this invention are made using well known chemical procedures. The required starting materials are commercially available, or readily synthesized utilizing standard procedures.

The compounds of formula (1) are, in general, prepared by treatment of about equimolar amounts of the corresponding pyridine substituted on the appropriate position with a suitable leaving group (e.g. halogen, alkylsulphonyl) with the corresponding hydroxymethyl-methoxyiminobenzeneacetamide to which was added an about equimolar amount or slight excess molar amount of a strong base, such as, for example, sodium hydride, in the presence of an inert solvent. The compound of formula (1) thus produced may optionally be modified by subsequent reaction to other desired compounds of formula (1).

The following examples further illustrate this invention. The examples should not be construed as limiting the invention in any manner.

EXAMPLES

Example 1

Methanone: phenyl-(5,6-dichloro-3-pyridyl)-,

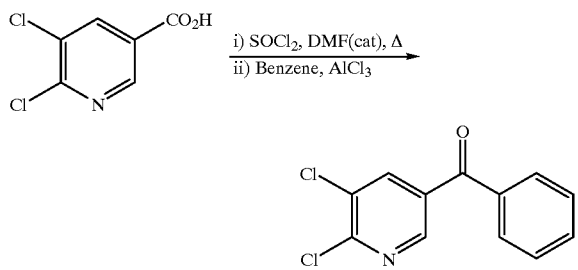

5,6-Dichloronicotinic acid (5.0 g, 0.026 mol) was slurried in 50 mL thionyl chloride and dimethylformamide (DMF) (2 drops) added. The mixture was then heated under reflux conditions for 1.5 hours. This was cooled and excess solvent thoroughly removed in vacuo. The acid chloride product was dissolved in anhydrous benzene (40 mL) and cooled to 0° C. in an ice bath under nitrogen. Aluminium trichloride (7.0 g, 0.052 mol) was added over 20 minutes and the mixture allowed to warm to room temperature under nitrogen overnight. The resulting biphasic mixture was diluted to 350 mL with ice water and extracted with ethyl acetate (3×50 mL). The organic extracts were combined and washed with 1N NaOH (2×150 mL), water (2×200 mL), and dried over magnesium sulfate. Evaporation of the solvent and recrystallisation of the residue from dichloromethane and hexane gave the product (4.83 g, 77% yield) as an off white solid, melting point 84–85° C.

Example 2

Nicotinamide: 5,6-dichloro-N-methoxy-N-methyl-,

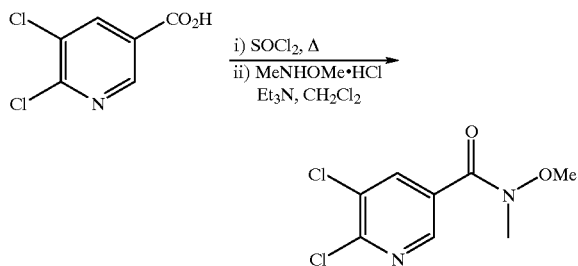

N,O-Dimethylhydroxylamine hydrochloride (2.25 g, 0.023 mol) was slurried in dichloromethane (40 mL) and cooled in ice-acetone. Triethylamine (4.7 g, 0.047 mol) was then added dropwise, followed by a solution of 5,6-dichloronicotinoyl chloride (4.5 g, 0.021 mol) in dichloromethane (25 mL). The resultant mixture was allowed to warm to room temperature and stirred for one hour. Water (50 mL) was added and the mixture separated. The organic phase was washed with water, 1M hydrochloric acid, 10% sodium carbonate solution and brine. It was then dried ($Na_2SO_4$) and evaporated to dryness to give the desired product (4.3 g, 86%) as a yellow oil which crystallized on standing.

Example 3

Methanone: phenyl-(5,6-dichloro-3-pyridyl)-,

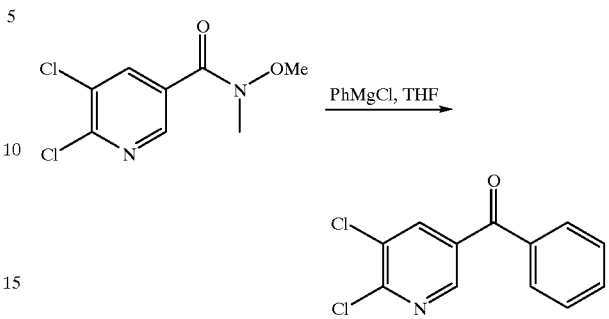

5,6-Dichloro-N-methoxy-N-methylnicotinamide (4.3 g, 0.018 mol) was dissolved with stirring in dry THF (80 mL) and cooled in ice-acetone to −10° C. Phenylmagnesium chloride (2M solution in THF, 20 mL) was added dropwise over 20 minutes and the mixture stirred at room temperature overnight. The reaction was quenched with saturated ammonium chloride (25 mL) and 2M hydrochloric acid (50 mL). The mixture was separated and the aqueous phase extracted with ether (2×50 mL). The organic extracts were combined and washed with water and brine, and dried ($Na_2SO_4$). Evaporation of the solvent and purification of the residue by chromatography over silica (0–25% ethyl acetate:pentane) gave the product (3.2 g, 69%) as a pale oil which crystallized on standing.

Example 4

Methanone: phenyl-(5-chloro-6-methylthio-3-pyridyl)-,

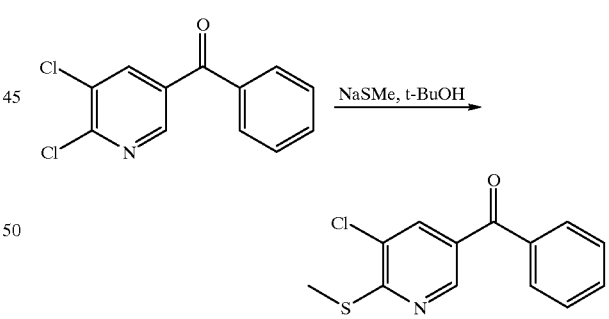

Phenyl-(5,6-dichloro-3-pyridyl)methanone (3.1 g, 0.0123 mol) was slurried in t-butanol (75 mL) and sodium methanethiolate (1.30 g, 0.0186 mol) added. The mixture was stirred at 40–45° C. overnight, poured into water and extracted with hexane (2×100 mL). The organic extracts were combined, washed with water and brine, and dried ($Na_2SO_4$). Evaporation of solvent and purification of the residue by chromatography over silica (2% ethyl acetate:hexane) gave the desired product (3.1 g, 95%) as a yellow oil.

Example 5

Dioxolane: 2-phenyl-2-(5-chloro-6-methylthio-3-pyridyl)-,

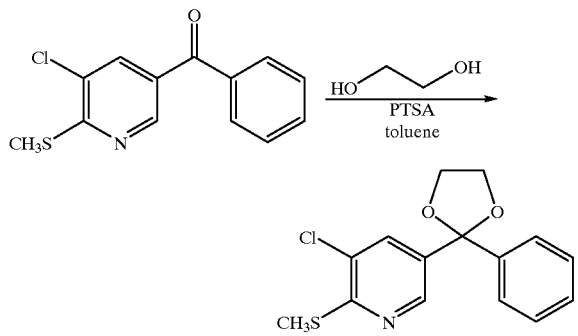

Phenyl-(5-chloro-6-methylthio-3-pyridyl)methanone (0.45 g, 1.7 mmol) was dissolved in 30 mL anhydrous toluene. Added 1.4 g (excess) ethylene glycol and 0.4 g (1.2 eq) para-toluenesulfonic acid (PTSA). Heated reaction mixture to reflux overnight using a Dean-Stark trap for azeotropic water removal. The reaction was poured into 250 mL water and extracted with 3×50 mL EtOAc; combined organics were washed with water, saturated brine, dried over magnesium sulfate, filtered, and evaporated to dryness to give 0.49 g (93.7%) product as a red syrup.

Example 6

Dioxolane: 2-phenyl-2-(5-chloro-6-methylsulfonyl-3-pyridyl)-,

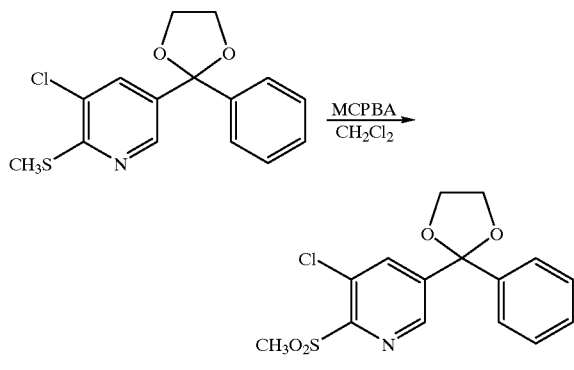

Dissolved 2-phenyl-2-(5-chloro-6-methylthio-3-pyridyl)-dioxolane (0.49 g, 1.59 mmol) in 20 mL methylene chloride and cooled to 0° C. Portionwise added 1.17 g (4 eq) meta-chloroperoxybenzoic acid (MCPBA) over 10 minutes and allowed to stir at room temperature overnight. Diluted to 250 mL with water and adjusted to pH 8–9 with 1 M sodium hydroxide; extracted aqueous layer with methylene chloride (3×50 mL) and washed organics with water and brine and dried ($Na_2SO_4$). Evaporation of solvent gave product (0.51 g, 95%) as a light yellow oil that solidified upon standing.

Example 7

Benzeneacetamide: 2-[[[3-chloro-5-(2-phenyl-1,3-dioxolan-2-yl)-2-pyridinyl]oxy]methyl]-α-(methoxyimino)-N-methyl-,

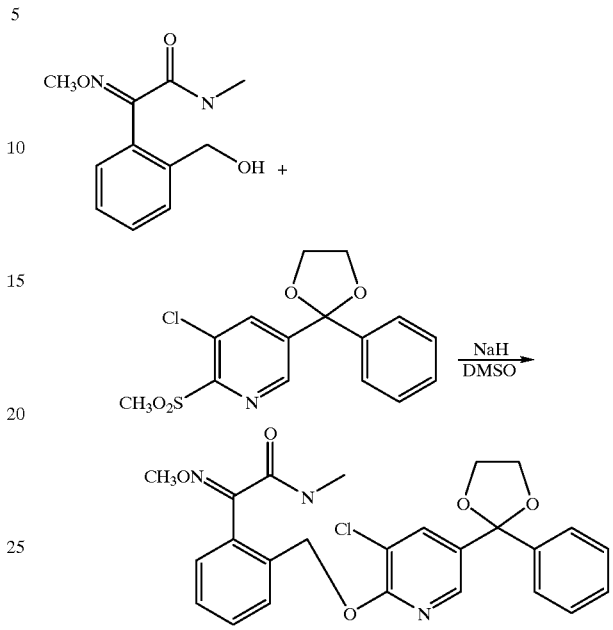

(2-Hydroxymethyl)-methoximinobenzeneacetamide (0.33 g, 1.5 mmol) was dissolved in 10 mL anhydrous dimethylsulfoxide (DMSO). Sodium hydride (60% in mineral oil, 0.1 g, 2.5 mmol) was added under nitrogen and the mixture was stirred at room temperature for ten minutes. 2-phenyl-2-(5-chloro-6-methylsulfonyl-3-pyridyl) dioxolane (0.5 g, 1.47 mmol) was added and the mixture stirred at room temperature for 1 hr. The mixture was diluted to 300 mL with water, extracted with methylene chloride (3×50 mL), washed with water and saturated brine, dried ($MgSO_4$), filtered, and evaporated to dryness to give the product (0.30 g, 41.5%) as a thick yellow oil after purification via chromatography over silica gel (30% ethyl acetate:pentane).

Example 8

6-Fluoro-5-methyl-3-pyridinemethanol: α-(1,1-dimethylethyl)-,

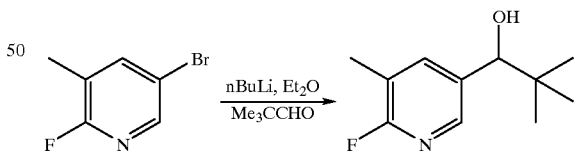

5-Bromo-2-fluoro-3-methylpyridine (2.0 g, 0.011 mol) was dissolved with stirring in anhydrous ether (30 mL) and cooled to −70° C. This was treated at <−60° C. with n-butyl lithium (4.8 mL, 2.5M in hexane, 0.012 mol) and the reaction mixture stirred at <−70° C. for one hour. Trimethylacetaldehyde (1.14 g, 0.013 mol) was added and the reaction mixture allowed to warm to −10° C. The reaction mixture was quenched with ammonium chloride solution and extracted with ethyl acetate. The organic extract was washed with water and brine, dried ($Na_2SO_4$) and evaporated to dryness. Purification of the residue by chromatography over silica (5–25% ethyl acetate:hexane) gave the desired product (1.6 g, 77%) as a clear oil.

Example 9

1-Propanone: 2,2-dimethyl-1-(6-fluoro-5-methyl-3-pyridinyl)-,

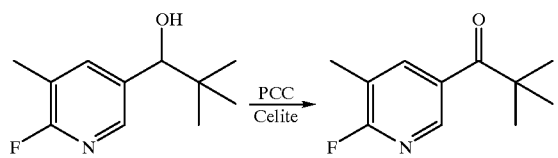

α-(1,1-Dimethylethyl)-6-fluoro-5-methyl-3-pyridinemethanol (1.6 g, 8.12 mmol) was dissolved with stirring in dichloromethane (50 mL) and celite (2.6 g) and pyridinium chlorochromate (2.63 g, 0.012 mol) added. The reaction mixture was stirred at room temperature overnight and filtered through celite, the solids being washed with dichloromethane (50 mL). The combined organic solutions were filtered through a column of silica gel, the product being eluted with dichloromethane. Evaporation of the solvent gave the desired product (1.5 g, 95%) as a clear oil which crystallized on standing.

Example 10

1-Propanone: 2,2-dimethyl-1-(5,6-dichloro-3-pyridinyl)-,

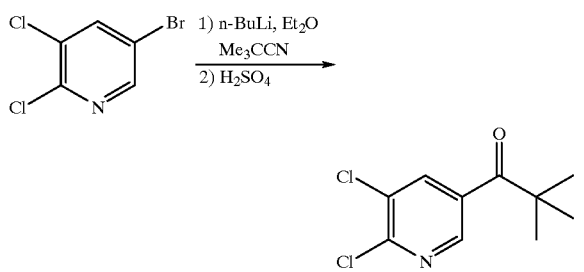

5-Bromo-2,3-dichloropyridine (2.27 g, 10 mmol) was dissolved in anhydrous ether (100 mL) in oven-dried glassware under nitrogen. The stirred solution was cooled in a Dry Ice-acetone bath (ca. −70° C.) and treated via syringe with n-butyllithium/hexane (2.5 M solution in hexane, 4 mL, 10 mmol) over 3 minutes. The resulting yellow-orange mixture was stirred in the cooling bath for 35 minutes, then was treated dropwise via syringe with pivalonitrile (1.33 mL, 12 mmol). Stirring was continued in the cooling bath for 1 hour and at ambient temperature for 1 hour. Then the mixture was cooled in an ice-water bath, and 2N sulphuric acid (35 mL) was added dropwise with efficient stirring. The resulting mixture was heated at reflux with stirring for 2 hours, and allowed to cool. The ether phase was separated, and the aqueous phase extracted with ether (2×30 mL). The combined ethereal solution was washed with saturated sodium bicarbonate solution, dried (MgSO$_4$), filtered and concentrated in vacuo, leaving 1.42 g of the crude product as a red oil. Purification by distillation, collecting the material distilling up to 110° C. at ca. 0.05 mm Hg, afforded 0.72 g (31%) of the desired product as a yellowish crystalline solid, m.p. 29–30° C.

Example 11

1-Propanone: 2,2-dimethyl-1-(5-methyl-6-methylthio-3-pyridinyl)-,

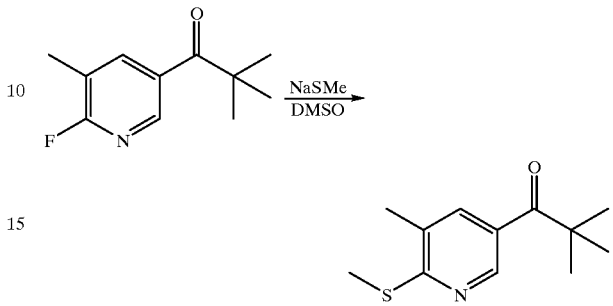

2,2-Dimethyl-1-(6-fluoro-5-methyl-3-pyridinyl)-1-propanone (1.0 g, 5.13 mmol) was dissolved with stirring in dimethyl sulphoxide (30 mL) and sodium methanethiolate (0.7 g, 0.01 mol) added. This was stirred at room temperature for 3 hours, poured into water, and extracted with hexane (2×30 mL). The organic extracts were combined, washed with water and brine, and dried (Na$_2$SO$_4$). Evaporation of the solvent gave the desired product (1.0 g, 87%) as a yellow oil.

Example 12

1,3-Dioxolane: 2-(2,2-dimethylethyl)-2-(5-methyl-6-methylthio-3-pyridinyl)-,

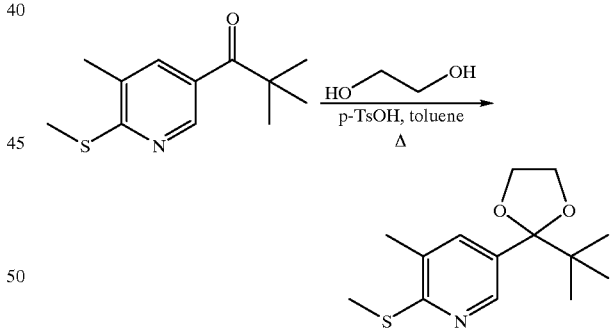

A mixture of 2,2-dimethyl-1(5-methyl-6-methylthio-3-pyridinyl)-1-propanone (0.80 g, 3.59 mmol), p-toluenesulphonic acid (0.75 g, 3.95 mmol), ethylene glycol (1.22 g, 0.018 mol) and toluene (50 mL) was heated under reflux under Dean & Stark conditions overnight. The mixture was cooled and washed with water, 2M sodium hydroxide solution, brine, and dried (Na$_2$So$_4$). Evaporation of the solvent under reduced pressure and purification of the residue by chromatography over silica (5% ethyl acetate:hexane) gave the desired product (0.68 g, 71%) as a clear oil.

Example 13
1,3-Dioxolane: 2-(2,2-dimethylethyl)-2-(5-methyl-6-methylsulphonyl-3-pyridinyl)-,

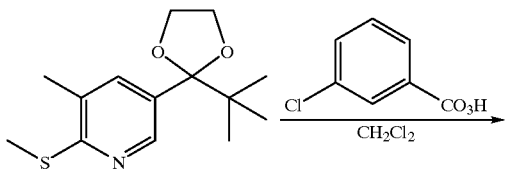

2-(2,2-Dimethylethyl)-2-(5-methyl-6-methylthio-3-pyridinyl)-1,3-dioxolane, (0.60 g, 2.24 mmol) was dissolved with stirring in dichloromethane (25 mL) and m-chloroperoxybenzoic acid (1.56 g, 55% assay, 5 mmol) added. The reaction mixture was stirred overnight and 2M sodium hydroxide solution (40 mL) added. The mixture was separated, the organic phase washed with 2M sodium hydroxide solution (2×25 mL), and dried (Na₂SO₄). Evaporation of the solvent under reduced pressure gave the desired product (0.62 g, 92%) as a clear oil.

Example 14
Benzeneacetamide: 2-[[[3-methyl-5-(2-(2,2-dimethylethyl)-1,3-dioxolan-2-yl)-2-pyridinyl]oxy]methyl]-α-(methoxyimino)-N-methyl-,

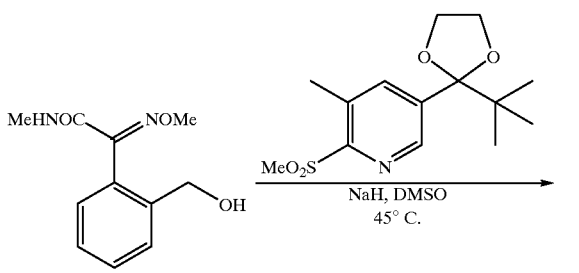

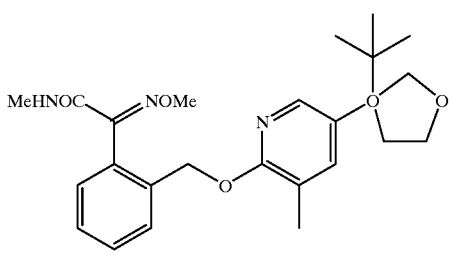

2-(Hydroxymethyl)-α-(methoxyimino)-N-methyl-benzeneacetamide (0.46 g, 2.07 mmol) was dissolved with stirring in anhydrous dimethyl sulphoxide (20 mL) and 60% sodium hydride (0.10 g, 2.5 mmol) added. The reaction mixture was stirred at room temperature for 20 minutes and a solution of 2-(2,2-dimethylethyl)-2-(5-methyl-6-methylsulphonyl-3-pyridinyl)-1,3-dioxolane (0.62 g, 2.07 mmol) in anhydrous dimethyl sulphoxide (5 mL) added. The reaction mixture was heated to 45° C. and stirred overnight. It was then cooled to room temperature and poured into water. This was extracted with ethyl acetate (2×40 mL), the organic extracts combined and washed with water and brine, and dried (Na₂SO₄). Evaporation of the solvent under reduced pressure and purification of the residue by chromatography over silica (10–50% ethyl acetate:pentane) gave the desired product (0.37 g, 40%) as a clear gum.

The following table identifies several compounds of the formula below, prepared analogous to the various procedures illustrated in the preceding examples:

TABLE 1

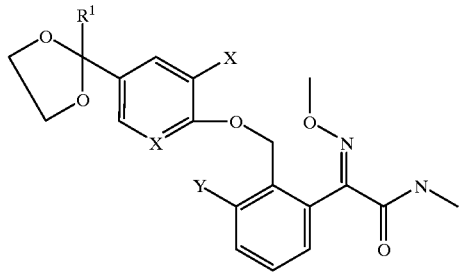

| Compound | Y  | X  | R¹                         |
|----------|----|----|----------------------------|
| 1        | H  | Cl | H                          |
| 2        | H  | Cl | Ph                         |
| 3        | F  | Cl | Ph                         |
| 4        | Cl | Cl | Ph                         |
| 5        | H  | Cl | Me                         |
| 6        | H  | Cl | Et                         |
| 7        | H  | Cl | 3-trifluoromethyl-phenyl   |
| 8        | H  | Cl | t-Bu                       |
| 9        | H  | Me | H                          |
| 10       | H  | H  | H                          |
| 11       | H  | Me | Me                         |
| 12       | H  | Me | t-Bu                       |
| 13       | H  | Me | Ph                         |
| 14       | H  | Me | 4-fluorophenyl             |
| 15       | H  | Me | 4-chlorophenyl             |
| 16       | H  | Cl | 4-trifluoromethoxy-phenyl  |
| 17       | H  | Me | 4-trifluoromethoxy-phenyl  |
| 18       | F  | Me | Ph                         |
| 19       | F  | Me | 4-fluorophenyl             |
| 20       | F  | Me | 4-chlorophenyl             |
| 21       | Cl | Me | 4-chlorophenyl             |
| 22       | Cl | Me | Ph                         |
| 23       | Cl | Me | 4-fluorophenyl             |

The compounds of formula (1) thus produced are usually obtained as a mixture of E and Z forms, which can then be separated into each of those forms, if desired by chromatography.

The compounds of formula (I) show strong fungicidal activity against a wide variety of fungi. The following tests illustrate the fungicidal efficacy of the compounds of this invention.

FUNGICIDE UTILITY

The compounds of the present invention have been found to control fungi, particularly plant pathogens. When employed in the treatment of plant fungal diseases, the compounds are applied to the plants in a disease inhibiting and phytologically acceptable amount. Application may be performed before and/or after the infection with fungi on plants. Application may also be made through treatment of seeds of plants, soil where plants grow, paddy fields for seedlings, or water for perfusion.

As used herein, the term "disease inhibiting and phytologically acceptable amount", refers to an amount of a compound of the present invention which kills or inhibits the plant disease for which control is desired, but is not significantly toxic to the plant. This amount will generally be from about 1 to 1000 ppm, with 10 to 500 ppm being preferred. The exact concentration of compound required varies with the fungal disease to be controlled, the type of formulation employed, the method of application, the particular plant species, climate conditions, and other factors. A suitable application rate is typically in the range from about 0.10 to about 4 lb/A.

The compounds of the invention may also be used to protect stored grain and other non-plant loci from fungal infestation.

The following experiments were performed in the laboratory to determine the fungicidal efficacy of the compounds of the invention.

Compound Formulation: Compound formulation was accomplished by dissolving technical materials in acetone, with serial dilutions then made in acetone to obtain desired rates. Final treatment volumes were obtained by adding nine volumes 0.05% aqueous Tween-20 or Triton X-100, depending upon the pathogen.

Powdery Mildew of Wheat (*Erysiphe graminis tritici*—ERYSGT) (48 hour curative) (2DC):

Wheat (*cultivar Monon*) was grown in a soilless peat-based potting mixture ("Metromix") until the seedlings were 10–20 cm tall. These plants were then inoculated with *Erysiphe graminis* by dusting spores from stock plants onto the test plants. After 48 hours the plants were sprayed to runoff with the test compound at a rate of 25 ppm and then kept in the greenhouse until disease developed on the untreated control plants.

Powdery Mildew of Wheat (*Erysiphe graminis tritici*—ERYSGT) (24 hour protectant) (1DP):

Wheat (*cultivar Monon*) was grown in a soilless peat-based potting mixture ("Metromix") until the seedlings were 10–20 cm tall. These plants were then sprayed to runoff with the test compound at a rate of 25 ppm. After 24 hours the test plants were inoculated with *Erysiphe graminis* by dusting spores from stock plants onto the test plants. The plants were then transferred to the greenhouse until disease developed on the untreated control plants.

The following table presents the activity of typical compound of the present invention when evaluated in these experiments. The effectiveness of the test compounds in controlling disease was rated using the following scale:

| Compound | ERYSGT 1DP 25 PPM | ERYSGT 2DC 25 PPM |
|---|---|---|
| 2 | ++ | ++ |
| 3 | + | ++ |
| 4 | + | ++ |
| 5 | + | ++ |
| 6 |  | ++ |
| 7 | ++ |  |
| 8 | + |  |
| 11 |  | ++ |
| 12 |  | ++ | blank space = not tested
− = 0–24% control of plant disease
+ = 25–74% control of plant disease
++ = 75–100% control of plant disease Brown Rust of Wheat (*Puccinia recondita*—PUCCRT) (48 hour curative) (2DC):

Wheat (*cultivar Monon*) was grown in a soilless peat-based potting mixture ("Metromix") until the seedlings were 10–20 cm tall. These plants were then inoculated by spraying with an aqueous spore suspension of *Puccinia recondita*. After 48 hours the plants were sprayed to runoff with the test compound at a rate of 25 ppm and then kept in the greenhouse until disease developed on the untreated control plants.

Brown Rust of Wheat (*Puccinia recondita*—PUCCRT) (24 hour protectant) (1DP):

Wheat (*cultivar Monon*) was grown in a soilless peat-based potting mixture ("Metromix") until the seedlings were 10–20 cm tall. These plants were then sprayed to runoff with the test compound at a rate of 25 ppm. After 24 hours the test plants were inoculated by spraying with an aqueous spore suspension of *Puccinia recondite*. The plants were then transferred to the greenhouse until disease developed on the untreated control plants.

The following table presents the activity of typical compounds of the present invention when evaluated in these experiments. The effectiveness of the test compounds in controlling disease was rated using the following scale:

| Compound | PUCCRT 1DP 25 PPM | PUCCRT 2DC 25 PPM |
|---|---|---|
| 2 | ++ |  |
| 3 | ++ |  |
| 4 | ++ |  |
| 5 | ++ |  | blank space = not tested
− = 0–24% control of plant disease
+ = 25–74% control of plant disease
++ = 75–100% control of plant disease Glume Blotch of Wheat (*Leptosphaeria nodorum*—LEPTNO) (24 hour protectant) (1DP):

Wheat (*cultivar Monon*) was grow in a soilless peat-based potting mixture ("Metromix") until the seedlings were 10–20 cm tall. These plants were then sprayed to runoff with the test compound at a rate of 25 ppm. After 24 hours the test plants were inoculated by spraying with an aqueous spore suspension of *Leptosphaeria nodorum*. The plants were then transferred to the greenhouse eveloped on the untreated control plants.

The following table presents the activity of typical compounds of the present invention when evaluated in these experiments. The effectiveness of the test compounds in controlling disease was rated using the following scale:

| Compound | LEPTNO 1DP 25 PPM |
|----------|-------------------|
| 2 | ++ |
| 3 | ++ |
| 4 | ++ |
| 5 | + | blank space = not tested
− = 0–24% control of plant disease
+ = 25–74% control of plant disease
++ = 75–100% control of plant disease Leaf blotch of Wheat (*Septoria tritici*—SEPTTR) (48 hour curative) (2DC):

Wheat (*cultivar Monon*) was grown in a soilless peat-based potting mixture ("Metromix") until the seedlings were 10–20 cm tall. These plants were inoculated by spraying with an aqueous spore suspension of *Septoria tritici*. After 48 hours the test plants were sprayed to runoff with the test compound at a rate of 25 ppm. The plants were then transferred to the greenhouse until disease developed on the untreated control plants.

Leaf blotch of Wheat (*Septoria tritici*—SEPTTR) (24 hour protectant) (1DP):

Wheat (*cultivar Monon*) was grown in a soilless peat-based potting mixture ("Metromix") until the seedlings were 10–20 cm tall. These plants were then sprayed to runoff with the test compound at a rate of 25 ppm. After 24 hours the test plants were inoculated by spraying with an aqueous spore suspension of *Septoria tritici*. The plants were then transferred to the greenhouse until disease developed on the untreated control plants.

The following table presents the activity of typical compounds of the present invention when evaluated in these experiments. The effectiveness of the test compounds in controlling disease was rated using the following scale:

| Compound | SEPTTR 1DP 25 PPM | SEPTTR 2DC 25 PPM |
|----------|-------------------|-------------------|
| 1 | + | |
| 2 | ++ | |
| 3 | ++ | |
| 4 | ++ | |
| 5 | ++ | |
| 6 | − | |
| 7 | ++ | |
| 8 | ++ | | blank space = not tested
− = 0–24% control of plant disease
+ = 25–74% control of plant disease
++ = 75–100% control of plant disease Dowly Mildew of Grape (*Plasmopara viticola*—PLASVI) (48 Hour Curative) (2DC):

Vines (*cultivar Carignane*) were grown from seed in a soilless peat-based potting mixture ("Metromix") until the seedlings were 10–20 cm tall. The test plants were inoculated by spraying with an aqueous sporangia suspension of *Plasmopara viticola*. After 48 hours the plants were sprayed to runoff with the test compound at a rate of 100 ppm and then kept in the greenhouse until disease developed on the untreated control plants.

Downy Mildew of Grape (*Plasmopara viticola*—PLASVI) (24 Hour Curative) (IDC):

Vines (*cultivar Carignane*) were grown from seed in a soilless peat-based potting mixture ("Metromix") until the seedlings were 10–20 cm tall. The test plants were inoculated by spraying with an aqueous sporangia suspension of *Plasmopara viticola*. After 24 hours the plants were sprayed to runoff with the test compound at a rate of 100 ppm and then kept in the greenhouse until disease developed on the untreated control plants.

Downy Mildew of Grape (*Plasmopara viticola*—PLASVI) (96 Hour Protectant) (4DP):

Vines (*cultivar Carignane*) were grown from seed in a soilless peat-based potting mixture ("Metromix") until the seedlings were 10–20 cm tall. These plants were then sprayed to runoff with the test compound at a rate of 100 ppm. After 96 hours the test plants were inoculated by spraying with an aqueous sporangia suspension of *Plasmopara viticola*. The plants were then transferred to the greenhouse until disease developed on the untreated control plants.

Downy Mildew of Grace (*Plasmopara viticola*—PLASVI) (240 Hour Protectant) (10DP):

Vines (*cultivar Carignane*) were grown from seed in a soilless peat-based potting mixture ("Metromix") until the seedlings were 10–20 cm tall. These plants were then sprayed to runoff with the test compound at a rate of 100 ppm. After 240 hours the test plants were inoculated by spraying with an aqueous sporangia suspension of *Plasmopara viticola*. The plants were then transferred to the greenhouse until disease developed on the untreated control plants.

The following table presents the activity of typical compounds of the present invention when evaluated in these experiments. The effectiveness of the test compounds in controlling disease was rated using the following scale:

| Compound | PLASVI 2DC 100 PPM | PLASVI 1DC 100 PPM | PLASVI 4DP 100 PPM | PLASVI 10DP 100 PPM |
|----------|-------------------|-------------------|-------------------|--------------------|
| 1 | − | | ++ | |
| 2 | ++ | | ++ | |
| 3 | + | | ++ | |
| 4 | − | | ++ | |
| 6 | | + | | ++ |
| 7 | | + | | ++ |
| 8 | | − | | ++ | blank space = not tested
− = 0–24% control of plant disease
+ = 25–74% control of plant disease
++ = 75–100% control of plant disease The compounds of this invention are preferably applied in the form of a composition comprising one or more of the compounds of formula (1) with a phytologically-acceptable carrier. The compositions are either concentrated formulations which are dispersed in water or another liquid for application, or are dust or granular formulations which are applied without further treatment. The compositions are prepared according to procedures which are conventional in the agricultural chemical art, but which are novel and important because of the presence therein of the compounds of this invention. Some description of the formulation of the compositions is given to assure that agricultural chemists can readily prepare desired compositions.

The dispersions in which the compounds are applied are most often aqueous suspensions or emulsions prepared from concentrated formulations of the compounds. Such water-soluble, water suspendable, or emulsifiable formulations are either solids, usually known as wettable powders, or liquids, usually known as emulsifiable concentrates or aqueous suspensions. The present invention contemplates all vehicles by which the compounds of this invention can be formulated for delivery for use as a fungicide. As will be readily appreciated, any material to which these compounds can be added may be used, provided they yield the desired utility without significant interference with activity of the compounds of this invention as antifungal agents.

Wettable powders, which may be compacted to form water dispersible granules, comprise an intimate mixture of the active compound, an inert carrier and surfactants. The concentration of the active compound is usually from about 10% to about 90% w/w, more preferably about 25% to about 75% w/w. In the preparation of wettable powder compositions, the toxicant products can be compounded with any of the finely divided solids, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier is ground or mixed with the toxicant in a volatile organic solvent. Effective surfactants, comprising from about 0.5% to about 10% of the wettable powder, include sulfonated lignins, naphthalenesulfonates, alkylbenzenesulfonates, alkyl sulfates, and non-ionic surfactants, such as ethylene oxide adducts of alkyl phenols.

Emulsifiable concentrates of the compounds of this invention comprise a convenient concentration, such as from about 10% to about 50% w/w, in a suitable liquid. The compounds are dissolved in an inert carrier, which is either a water miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, such as, for example, terpenic solvents, including rosin derivatives, aliphatic ketones, such as cyclohexanone, and complex alcohols, such as 2-ethoxyethanol.

Emulsifiers which can be advantageously employed herein can be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyoxyalkylene. Cationic emulsifiers include quaternary ammonium compounds and fatty amine salts. Anionic emulsifiers include the oil-soluble salts (e.g., calcium) of alkylaryl sulphonic acids, oil soluble salts or sulphated polyglycol ethers and appropriate salts of phosphated polyglycol ether.

Representative organic liquids which can be employed in preparing the emulsifiable concentrates of the present invention are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides of fatty glycols and glycol derivatives such as the n-butyl ether, ethyl ether or methyl ether of diethylene glycol, and the methyl ether of triethylene glycol. Mixtures of two or more organic liquids are also often suitably employed in the preparation of the emulsifiable concentrate. The preferred organic liquids are xylene, and propyl benzene fractions, with xylene being most preferred. The surface active dispersing agents are usually employed in liquid compositions and in the amount of from 0.1 to 20 percent by weight of the combined weight of the dispersing agent and active compound. The active compositions can also contain other compatible additives, for example, plant growth regulators and other biologically active compounds used in agriculture.

Aqueous suspensions comprise suspensions of water-insoluble compounds of this invention, dispersed in an aqueous vehicle at a concentration in the range from about 5% to about 50% w/w. Suspensions are prepared by finely grinding the compound, and vigorously mixing it into a vehicle comprised of water and surfactants chosen from the same types above discussed. Inert ingredients, such as inorganic salts and synthetic or natural gums, may also be added to increase the density and viscosity of the aqueous vehicle. It is often most effective to grind and mix the compound at the same time by preparing the aqueous mixture and homogenizing it in an implement such as a sand mill, ball mill, or piston-type homogenizer.

The compounds may also be applied as granular compositions, which are particularly useful for applications to the soil. Granular compositions usually contain from about 0.5% to about 10% w/w of the compound, dispersed in an inert carrier which consists entirely or in large part of coarsely divided attapulgite, bentonite, diatomite, clay or a similar inexpensive substance. Such compositions are usually prepared by dissolving the compound in a suitable solvent and applying it to a granular carrier which has been preformed to the appropriate particle size, in the range of from about 0.5 to about 3 mm. Such compositions may also be formulated by making a dough or paste of the carrier and compound, and crushing and drying to obtain the desired granular particle Dusts containing the compounds are prepared simply by intimately mixing the compound in powdered form with a suitable dusty agricultural carrier, such as, for example, kaolin clay, ground volcanic rock, and the like. Dusts can suitably contain from about 1% to about 10% w/w of the compound.

The active compositions may contain adjuvant surfactants to enhance deposition, wetting and penetration of the compositions onto the target crop and organism. These adjuvant surfactants may optionally be employed as a component of the formulation or as a tank mix. The amount of adjuvant surfactant will vary from 0.01 percent to 1.0 percent v/v based on a spray-volume of water, preferably 0.05 to 0.5 percent. Suitable adjuvant surfactants include ethoxylated nonyl phenols, ethoxylated synthetic or natural alcohols, salts of the esters or sulphosuccinic acids, ethoxylated organosilicones, ethoxylated fatty amines and blends of surfactants with mineral or vegetable oils.

The composition may optionally include fungicidal combinations which comprise at least 1% of one or more of the compounds of this invention with another pesticidal compound. Such additional pesticidal compounds may be fungicides, insecticides, nematocides, miticides, arethropodicides, bactericides or combinations thereof that are compatible with the compounds of the present invention in the medium selected for application, and not antagonistic to the activity of the present compounds. Accordingly, in such embodiments the other pesticidal compound is employed as a supplemental toxicant for the same or for a different pesticidal use. The compounds in combination can generally be present in a ratio of from 1:100 to 100:1

The present invention includes within its scope methods for the control or prevention of fungal attack. These methods comprise applying to the locus of the fungus, or to a locus in which the infestation is to be prevented (for example applying to cereal or grape plants), a fungicidal amount of one or more of the compounds of this invention or compositions. The compounds are suitable for treatment of various plants at fungicidal levels, while exhibiting low phytotoxicity. The compounds are useful in a protectant or eradicant fashion. The compounds of this invention are applied by any of a variety of known techniques, either as the compounds or as compositions including the compounds. For example, the compounds may be applied to the roots, seeds or foliage of plants for the control of various fungi, without damaging the commercial value of the plants. The materials are applied in the form of any of the generally used formulation types, for example, as solutions, dusts, wettable powders, flowable concentrates, or emulsifiable concentrates. These materials are conveniently applied in various known fashions.

The compounds of this invention have been found to have significant fungicidal effect particularly for agricultural use. Many of the compounds are particularly effective for use with agricultural crops and horticultural plants, or with wood, paint, leather or carpet backing.

In particular, the compounds effectively control a variety of undesirable fungi which infect useful plant crops. Activity has been demonstrated for a variety of fungi, including for example the following representative fungi species: Downy Mildew of Grape (*Plasmopara viticola*—PLASVI), Late Blight of Tomato (*Phytophthora infestans*—PHYTIN), Apple Scab (*Venturia inaequalis*—VENTIN), Brown Rust of Wheat (*Puccinia recondita*—PUCCRT), Stripe Rust of Wheat (*Puccinia striiformis*—PUCCST), Rice Blast (*Pyricularia oryzae*—PYRIOR), Cercospora Leaf Spot of Beet (*Cercospora beticola*—CERCBE), Powdery Mildew of Wheat (*Erysiphe graminis*—ERYSGT), Leaf Blotch of Wheat (*Septoria tritici*—SEPTTR), Sheath Blight of Rice (*Rhizoctonia solani*—RHIZSO), Eyespot of Wheat (*Pseudocercosporella herpotrichoides*—PSDCHE), Brown Rot of Peach (*Monilinia fructicola*—MONIFC), Glume Blotch of Wheat (*Septoria nodorum*—LEPTNO). It will be understood by those in the art that the efficacy of the compounds of this invention for the foregoing fungi establishes the general utility of the compounds as fungicides.

The compounds of this invention have broad ranges of efficacy as fungicides. The exact amount of the active material to be applied is dependent not only on the specific active material being applied, but also on the particular action desired, the fungal species to be controlled, and the stage of growth thereof, as well as the part of the plant or other product to be contacted with the toxic active ingredient. Thus, all the active ingredients of the compounds of this invention, and compositions containing the same, may not be equally effective at similar concentrations or against the same fungal species. The compounds of this invention and compositions are effective in use with plants in a disease inhibiting and phytologically acceptable amount.

What is claimed is:

1. A compound of the formula

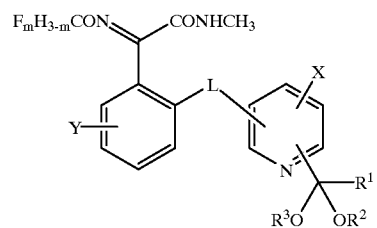

wherein m is an integer 0–3;

Y is H, halogen, $C_{1-4}$ alkyl, halo-$C_{1-4}$ alkyl, $C_{1-4}$ alkoxy, halo-$C_{1-4}$ alkoxy, or $C_{1-4}$ alkylthio;

X is H, $C_{1-6}$ alkyl, $C_{1-6}$ alkoxy, halo-$C_{1-6}$ alkyl, halo-$C_{1-6}$ alkoxy, halo, nitro, $C_{1-6}$ alkoxycarbonyl, cyano, $C_{1-6}$ alkylthio, or halo-$C_{1-6}$ alkylthio;

$R^1$ is H, $C_{1-6}$ alkyl optionally substituted with one or more halogens, $C_{3-7}$ cycloalkyl optionally substituted with one or more halogens, $C_{2-6}$ alkenyl, $C_{2-6}$ alkynyl, or phenyl wherein said phenyl is optionally substituted by one or more of any of the groups selected from halogens, $C_{1-6}$ alkyl, $C_{3-7}$ cycloalkyl, halo-$C_{1-6}$ alkoxy, $C_{2-6}$ alkenyl, halo-$C_{2-6}$ alkenyl, $C_{2-6}$ alkynyl, cyano, $C_{1-6}$ alkoxy, nitro, phenyl or phenyl substituted with one or more of $C_{1-6}$ alkyl, $C_{1-6}$ alkoxy, halo-$C_{1-6}$ alkyl, halo-$C_{1-6}$ alkoxy, halo, nitro, $C_{1-6}$ alkoxycarbonyl, or cyano;

$R^2$, $R^3$ together form a $C_{2-6}$ optionally substituted alkylene chain, wherein the optional substitution of the alkylene chain is with one or more of any of the following groups, $C_{1-4}$ alkyl optionally substituted with one or more halogens; or a phenyl group optionally substituted with one or more of any of the following groups, $C_{1-6}$ alkyl, $C_{1-6}$ alkoxy, halo-$C_{1-6}$ alkyl, halo-$C_{1-6}$ alkoxy, halo, nitro, $C_{1-6}$ alkoxycarbonyl, or cyano; and L is —O—, —$CH_2$—, —$SO_n$—, —$CH_2O$—, —$OCH_2$—, —$CH_2S$—, —$SCH_2$—, —CH=CH—, —C≡C—, or

wherein n is an integer 0–2.

2. The compound of claim 1 of the formula

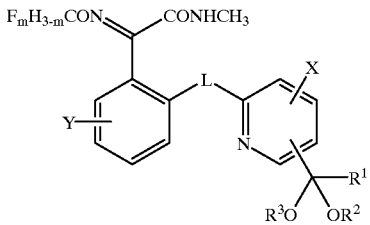

wherein the substituents are as defined in claim 1.

3. The compound of claim 2 of the formula

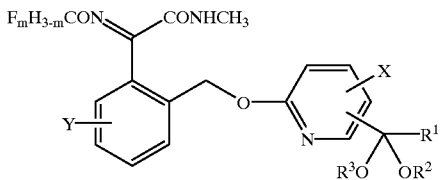

wherein the substituents are as defined in claim 1.

4. The compound of claim 3 of the formula

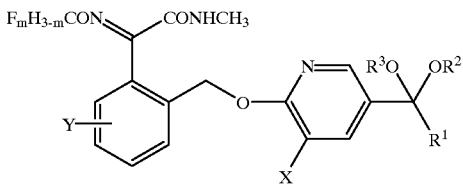

wherein the substituents are as defined in claim 1.

5. The compound of claim 4 of the formula

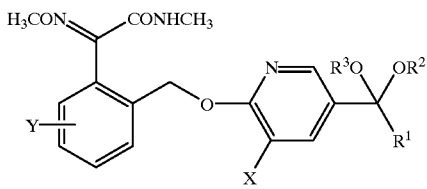

wherein the substituents are as defined claim in 1.

6. The compound of claim 5 of the formula

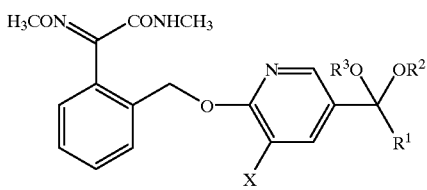

wherein the substituents are as defined in claim 1.

7. The compound of claim 1 of the formula

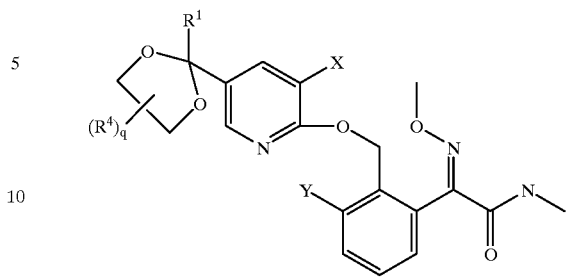

wherein the X, Y and $R^1$ substituents are as defined in claim 1; and $R^4$ is a $C_{1-4}$ alkyl optionally substituted with one or more halogens, or a phenyl group optionally substituted with one or more of any of the following groups, $C_{1-6}$ alkyl, $C_{1-6}$ alkoxy, halo-$C_{1-6}$ alkyl, halo-$C_{1-6}$ alkoxy, halo, nitro, $C_{1-6}$ alkoxycarbonyl, or cyano; and q is an integer of 0–4.

8. The compound of claim 7 wherein X, Y, and $R^1$ are as defined in claim 7 and q is 0.

9. The compound of claim 8 wherein

Y is H, F or Cl;

X is H, Cl or Me; and $R^1$ is H, $C_{1-6}$ alkyl or a phenyl optionally substituted with one or more of any of the following, Cl, F, $C_{1-6}$ alkyl, $C_{1-6}$ alkoxy, halo-$C_{1-6}$ alkyl, or halo-$C_{1-6}$ alkoxy.

10. The compound of claim 9 wherein $R^1$ is H, $C_{1-6}$ alkyl or a phenyl optionally substituted with one or more Cl, F, trifluoromethyl or trifluoromethoxy groups.

11. The compound of claim 6 of the formula

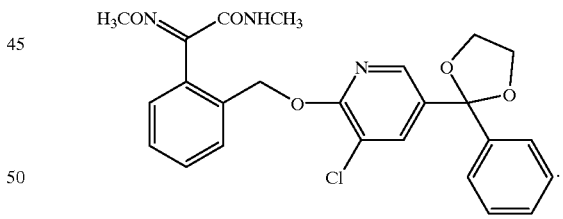

12. The compound of claim 6 of the formula

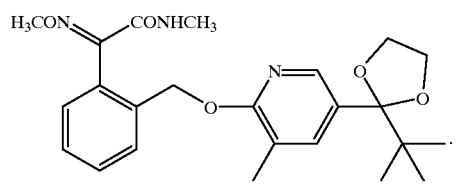

13. A fungicidal method which comprises applying to the locus to be treated a fungicidally-effective amount of a compound of the formula

23

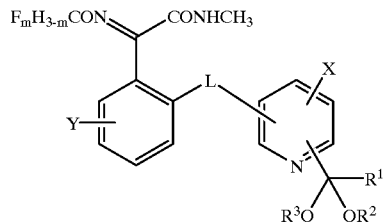

wherein
  m is an integer 0–3;
  Y is H, halogen, $C_{1-4}$ alkyl, halo-$C_{1-4}$ alkyl, $C_{1-4}$ alkoxy, halo-$C_{1-4}$ alkoxy, or $C_{1-4}$ alkylthio;
  X is H, $C_{1-6}$ alkyl, $C_{1-6}$ alkoxy, halo-$C_{1-6}$ alkyl, halo-$C_{1-6}$ alkoxy, halo, nitro, $C_{1-6}$ alkoxycarbonyl, cyano, $C_{1-6}$ alkylthio, or halo-$C_{1-6}$ alkylthio;
  $R^1$ is H, $C_{1-6}$ alkyl optionally substituted with one or more halogens, $C_{3-7}$ cycloalkyl optionally substituted with one or more halogens, $C_{2-6}$ alkenyl, $C_{2-6}$ alkynyl, or phenyl wherein said phenyl is optionally substituted by one or more of any of the groups selected from halogens, $C_{1-6}$ alkyl, $C_{3-7}$ cycloalkyl, halo-$C_{1-6}$ alkoxy, $C_{2-6}$ alkenyl, halo-$C_{2-6}$ alkenyl, $C_{2-6}$, alkynyl, cyano, $C_{1-6}$ alkoxy, nitro, phenyl or phenyl substituted with one or more of $C_{1-6}$ alkyl, $C_{1-6}$ alkoxy, halo-$C_{1-6}$ alkyl, halo-$C_{1-6}$ alkoxy, halo, nitro, $C_{1-6}$ alkoxycarbonyl, or cyano;
  $R^2$, $R^3$ together form a $C_{2-6}$ optionally substituted alkylene chain, wherein the optional substitution of the alkylene chain is with one or more of any of the following groups, $C_{1-4}$ alkyl optionally substituted with one or more halogens; or a phenyl group optionally substituted with one or more of any of the following groups, $C_{1-6}$ alkyl, $C_{1-6}$ alkoxy, halo-$C_{1-6}$ alkyl, halo-$C_{1-6}$ alkoxy, halo, nitro, $C_{1-6}$ alkoxycarbonyl, or cyano; and
  L is —O—, —CH$_2$—, —SO$_n$—, —CH$_2$O—, —OCH$_2$—, —CH$_2$S—, —SCH$_2$—, —CH=CH—, —C≡C—, or

, wherein n is an integer 0–2.

14. A fungicidal composition comprising a phytologically-acceptable carrier and a fungicidally effective amount of a compound of the formula

24

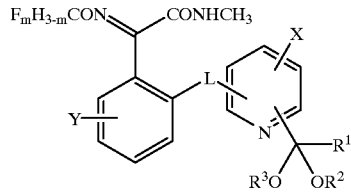

wherein
  m is an integer 0–3;
  Y is H, halogen, $C_{1-4}$ alkyl, halo-$C_{1-4}$ alkyl, $C_{1-4}$ alkoxy, halo-$C_{1-4}$ alkoxy, or $C_{1-4}$ alkylthio;
  X is H, $C_{1-6}$ alkyl, $C_{1-6}$ alkoxy, halo-$C_{1-6}$ alkyl, halo-$C_{1-6}$ alkoxy, halo, nitro, $C_{1-6}$ alkoxycarbonyl, cyano, $C_{1-6}$ alkylthio, or halo-$C_{1-6}$ alkylthio;
  $R^1$ is H, $C_{1-6}$ alkyl optionally substituted with one or more halogens, $C_{3-7}$ cycloalkyl optionally substituted with one or more halogens, $C_{2-6}$ alkenyl, $C_{2-6}$ alkynyl, or phenyl wherein said phenyl is optionally substituted by one or more of any of the groups selected from halogens, $C_{1-6}$ alkyl, $C_{3-7}$ cycloalkyl, halo-$C_{1-6}$ alkoxy, $C_{2-6}$ alkenyl, halo-$C_{2-6}$ alkenyl, $C_{2-6}$ alkynyl, cyano, $C_{1-6}$ alkoxy, nitro, phenyl or phenyl substituted with one or more of $C_{1-6}$ alkyl, $C_{1-6}$ alkoxy, halo-$C_{1-6}$ alkyl, halo-$C_{1-6}$ alkoxy, halo, nitro, $C_{1-6}$ alkoxycarbonyl, or cyano;
  $R^2$, $R^3$ together form a $C_{2-6}$ optionally substituted alkylene chain, wherein the optional substitution of the alkylene chain is with one or more of any of the following groups, $C_{1-4}$ alkyl optionally substituted with one or more halogens; or a phenyl group optionally substituted with one or more of any of the following groups, $C_{1-6}$ alkyl, $C_{1-6}$ alkoxy, halo-$C_{1-6}$ alkyl, halo-$C_{1-6}$ alkoxy, halo, nitro, $C_{1-6}$ alkoxycarbonyl, or cyano; and
  L is —O—, —CH$_2$—, —SO$_n$—, —CH$_2$O—, —OCH$_2$—, —CH$_2$S—, —SCH$_2$—, —CH=CH—, —C≡C—, or

, wherein n is an integer 0–2.

* * * * *